(12) United States Patent  
Harrison et al.

(10) Patent No.: US 9,347,933 B2  
(45) Date of Patent: May 24, 2016

(54) SYSTEM AND METHOD TO IMPROVE YIELD OF SORTED PARTICLES

(71) Applicant: BECTON, DICKINSON AND COMPANY, Franklin Lakes, NJ (US)

(72) Inventors: C. Brent Harrison, Seattle, WA (US); Andrew Lister, Bainbridge Island, WA (US); Valdis Janis Riekstins, Woodinville, WA (US); Willem Stokdijk, Seattle, WA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 176 days.

(21) Appl. No.: 14/364,057

(22) PCT Filed: Dec. 14, 2012

(86) PCT No.: PCT/US2012/069924  
§ 371 (c)(1),  
(2) Date: Jun. 9, 2014

(87) PCT Pub. No.: WO2013/096137  
PCT Pub. Date: Jun. 27, 2013

(65) Prior Publication Data  
US 2014/0322748 A1 Oct. 30, 2014

Related U.S. Application Data

(60) Provisional application No. 61/578,105, filed on Dec. 20, 2011.

(51) Int. Cl.  
*G01N 33/48* (2006.01)  
*G01N 31/00* (2006.01)  
(Continued)

(52) U.S. Cl.  
CPC ........ *G01N 33/5005* (2013.01); *G01N 15/1429* (2013.01); *G01N 15/1459* (2013.01);  
(Continued)

(58) Field of Classification Search  
CPC ....... G01N 15/06; G01N 33/00; G01N 33/48; G01N 31/00; G01N 35/00; G01N 1/18  
USPC ........ 422/50, 68.1, 73, 81, 82, 502, 503, 504, 422/509; 436/43, 180, 63, 174, 177  
See application file for complete search history.

(56) References Cited

U.S. PATENT DOCUMENTS 3,710,933 A 1/1973 Fulwyler et al.  
4,981,580 A 1/1991 Auer  
(Continued)

FOREIGN PATENT DOCUMENTS

CN 102119212 A 7/2011

*Primary Examiner* — Brian J Sines  
(74) *Attorney, Agent, or Firm* — Bret E. Field; Bozicevic, Field & Francis LLP

(57) ABSTRACT

Provided herein are systems and methods for improving yield of sorted particles. In one embodiment, for example, there is provided a system including: (a) a flow cytometer to analyze a sample, wherein the flow cytometer provides a parameter plot based on the analysis of the sample; (b) a user-interface, wherein a user can define a coincidence acceptance gate in the parameter plot, and wherein the coincidence acceptance gate identifies a non-target particle population in the sample that may be accepted with a target particle in a subsequent sort analysis; and (c) a sort analysis system to sort particles within the sample, while accepting particles defined by coincidence acceptance gate.

14 Claims, 4 Drawing Sheets

(51) Int. Cl.
  *G01N 35/00* (2006.01)
  *G01N 1/18* (2006.01)
  *G01N 33/50* (2006.01)
  *G01N 15/14* (2006.01)

(52) U.S. Cl.
  CPC .. *G01N2015/1402* (2013.01); *G01N 2015/149* (2013.01); *G01N 2015/1477* (2013.01); *G01N 2015/1488* (2013.01)

(56) References Cited

U.S. PATENT DOCUMENTS

| | | |
|---|---|---|
| 5,998,212 A | 12/1999 | Corio et al. |
| 6,281,018 B1 | 8/2001 | Kirouac et al. |
| 7,713,687 B2 * | 5/2010 | Seidel et al. ............ 435/2 |
| 7,758,811 B2 * | 7/2010 | Durack et al. ............ 422/73 |
| 7,855,078 B2 * | 12/2010 | Evans ............ 436/63 |
| 7,996,188 B2 | 8/2011 | Olson et al. |
| 8,004,661 B2 * | 8/2011 | Luscher ............ 356/72 |
| 8,665,439 B2 * | 3/2014 | Luscher ............ 356/417 |
| 8,820,538 B1 * | 9/2014 | Lin ............ 209/552 |
| 8,828,210 B2 * | 9/2014 | Abell et al. ............ 204/556 |
| 8,951,474 B2 * | 2/2015 | Takeda ............ 422/82.08 |
| 9,134,220 B2 * | 9/2015 | Malachowski et al. |
| 9,140,645 B2 * | 9/2015 | Merchez et al. |
| 2008/0228444 A1 * | 9/2008 | Olson et al. ............ 702/189 |
| 2008/0255705 A1 | 10/2008 | Degeal et al. |
| 2010/0090677 A1 | 4/2010 | Britton et al. |
| 2011/0010144 A1 | 1/2011 | Fox et al. |
| 2011/0269175 A1 | 11/2011 | Durack et al. |

\* cited by examiner

SYSTEM AND METHOD TO IMPROVE YIELD OF SORTED PARTICLES

CROSS-REFERENCE TO RELATED APPLICATIONS

Pursuant to 35 U.S.C. §119 (e) this application claims priority to the filing date of U.S. Provisional Patent Application Ser. No. 61/578,105 filed Dec. 20, 2011; the disclosure of which application is herein incorporated by reference.

The present invention relates to laboratory instruments such as flow cytometers. More specifically, the present invention relates to systems and methods for improving yield of sorted particles in a laboratory instrument.

Flow cytometers, for example, are valuable laboratory instruments for the analysis and isolation of biological particles, such as cells and constituent molecules. Flow cytometers utilize a fluid stream to linearly segregate particles such that they can pass, single file, through a detection apparatus measuring light scattering and/or fluorescence. Individual cells can then be characterized according to their scattering and the presence of detectable markers. Thus, a flow cytometer can be used to produce a diagnostic profile of a population of biological particles.

Current commercial flow cytometer sorter systems use a simple mechanism of thresholding to define a lower analysis limit. In practice, thresholding limits are typically set based on one of two modes: 1) a "high yield" mode, which deemphasizes purity in exchange for sorting a high number of target particles; or 2) a "high purity" mode, which deemphasizes yield in exchange for sorting a "purer" sample of target particles.

In some instances, currently available systems may be set to threshold on more than one parameter, but do not define (in a method consistent with normal sort gating logic) populations that are detected (above any threshold or combination of thresholds set) but that can safely be ignored, or otherwise accepted, in making sort decisions. As a consequence, target particles may not be sorted (or attempted to be sorted) due to their relative coincidence with other non-target particles, even though in some instances there is no functional disadvantage to the inclusion of such non-target particles. The net result is a reduction in yield of target particles, in an otherwise correctly functioning cytometer. This effect will be particularly significant when attempting to sort rare target populations, especially at higher sort rates approaching the normal practical limits of efficiency for any given set of sort conditions.

SUMMARY

Provided herein are systems and methods for improving yield of sorted particles. In one embodiment, for example, there is provided a system including: (a) a flow cytometer to analyze a sample, wherein the flow cytometer provides a parameter plot based on the analysis of the sample; (b) a user-interface, wherein a user can define a coincidence acceptance gate in the parameter plot, and wherein the coincidence acceptance gate identifies a non-target particle population in the sample that may be accepted with a target particle in a subsequent sort analysis; and (c) a sort analysis system to sort target particles within the sample, while accepting non-target particles defined by the coincidence acceptance gate.

The systems and methods disclosed provide a special user-definable population or class of sort region that is explicitly accepted, or otherwise ignored, in making sort decisions in flow cytometry. This new class may be viewed as a "coincidence acceptance gate," "a population of disinterest," "region of indifference," or "null sort gate." This user-definable population can consist of one or more regions defined on a data histogram. In the case that more than one region is used to define different sub-populations, they will be combined by a combination of logical AND/OR operators, or other Boolean operators. In some instances, the user is permitted to define population(s) of non-target particles that are detected by the flow cytometer, but that would not be deleterious to experimental outcome if included in a sorted population of desired target particles. Example populations of acceptable coincidence may include sub-cellular debris, or reference particles (e.g., marker beads) spiked into a biological preparation.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use systems and methods in accordance with the present invention.

DETAILED DESCRIPTION

Provided herein are systems and methods for improving yield of sorted particles. In one embodiment, for example, there is provided a system including: (a) a flow cytometer to analyze a sample, wherein the flow cytometer provides a parameter plot based on the analysis of the sample; (b) a user-interface, wherein a user can define a coincidence acceptance gate in the parameter plot, and wherein the coincidence acceptance gate identifies a non-target particle population in the sample that may be accepted with a target particle in a subsequent sort analysis; and (c) a sort analysis system to sort target particles within the sample, while accepting non-target particles defined by the coincidence acceptance gate.

The systems and methods disclosed provide a special user-definable population or class of sort region that is explicitly accepted, or otherwise ignored, in making sort decisions in flow cytometry. This new class may be viewed as a "coincidence acceptance gate," "a population of disinterest," "region of indifference," or "null sort gate." This user-definable population can consist of one or more regions defined on a data histogram. In the case that more than one region is used to define different sub-populations, they will be combined by a combination of logical AND/OR operators, or other Boolean operators. In some instances, the user is permitted to define population(s) of non-target particles that are detected by the flow cytometer, but that would not be deleterious to experimental outcome if included in a sorted population of desired target particles. Example populations of acceptable coincidence may include sub-cellular debris, or reference particles (e.g., marker beads) spiked into a biological preparation.

Figure 1:
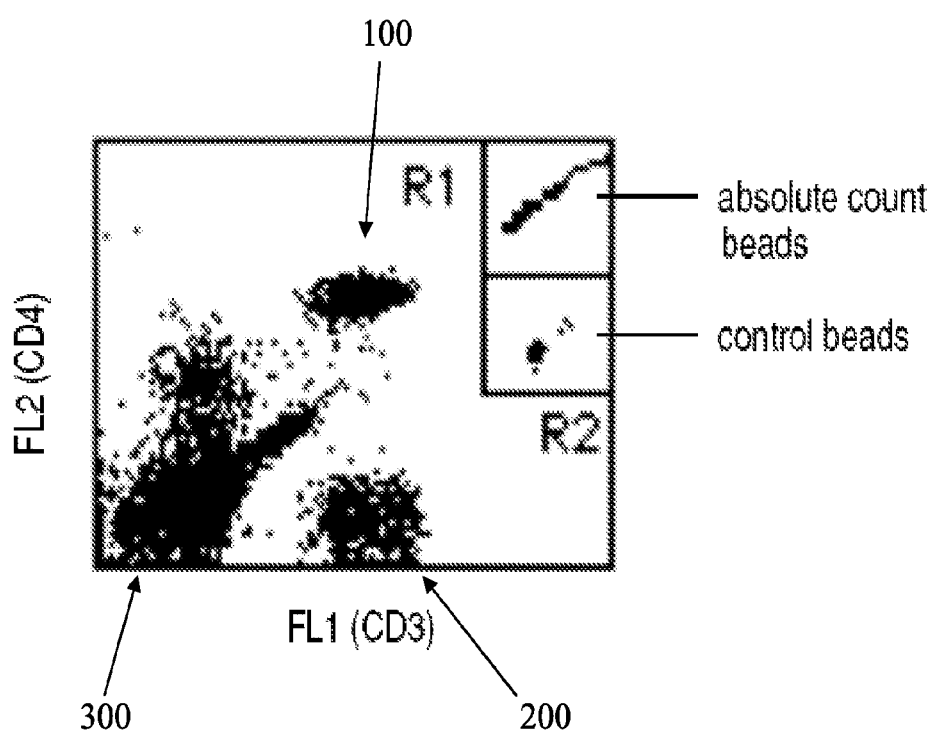
FIG. 1 shows an example of an un-gated FL1 (CD3) vs. FL2 (CD4) dot plot, showing counting bead and control bead regions.

FIG. 1 shows an example of an un-gated FL1 (CD3) vs. FL2 (CD4) dot plot, showing counting bead and control bead regions. In FIG. 1, a biological sample has been "spiked" with two types of reference beads, which fall into distinct regions R1 and R2 and do not impinge upon the cell population. In a typical sorting scenario, it might be desired to sort the population 100 and population 200 with high purity (i.e., with a high purity gate/mode), separating each of them from the other cellular components. With current sort methodology, when sorting for purity (rather than for yield, where every occurrence of a target event should be sorted), if a target particle is likely to be contained in a drop with another event of a different category, then the drop will not be sorted. Depending upon precise sort mode settings, this may even occur if the "contaminating event" is in an adjacent drop to the one expected to contain the target particle. The result is a loss of yield of sorted target particles, for no valid reason.

In the example shown in FIG. 1, the beads in R1 and R2 would not have any practical consequence upon the downstream (i.e., post-sort) processing, and so could be allowed to be sorted along with the target particles. As such, the present invention provides a means for a user to define a particle population (e.g., R1 and/or R2) of acceptable coincidence. The presented "coincidence acceptance gate" is thus an intermediary between a "yield gate" and a "purity gate," and allows the coincidence of non-target particles that have no (or limited) consequence when included with sorted target particles.

Figure 2:
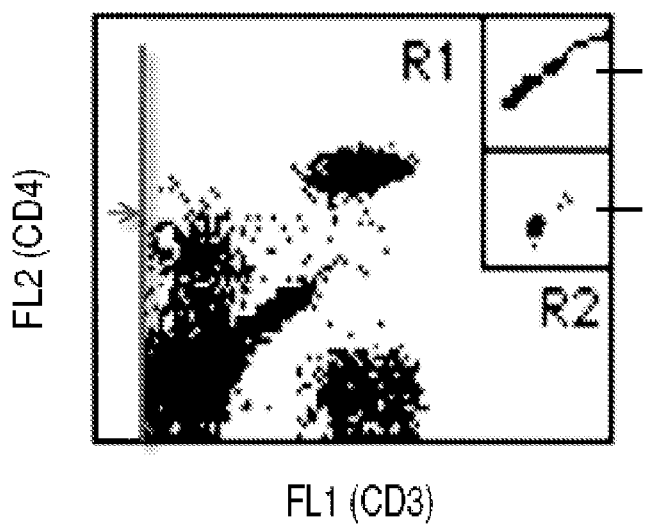
FIG. 2 illustrates thresholding by simulating an increase in threshold on the FL1 parameter.

Current technology does permit thresholding, though normally implemented on a scatter parameter. FIG. 2 illustrates thresholding by simulating an increase in threshold on the FL1 parameter. The effect is not only to remove the events from the particular display, making them invisible to the operator, they are also completely invisible to the instrument, and so ignored in any sort decision. The systems and methods presented extend and develop this idea, but without hiding the events, and with far greater flexibility in defining these permissible events. The systems and methods presented allow the user to define a population (or a series of populations) that can be safely ignored in sort logic processing, thereby improving overall sort yields of the important target-particles.

In alternative embodiments, an acceptance coincidence gate can be set on multiple regions defined on different parameters. For example, in one embodiment, firmware is implemented to allow for acceptance regions to be combined by a single logical OR gate or a single AND gate. In another embodiment, the acceptable coincidence events fall into two or more categories that are each defined by a combination of gates. For example, if S1 and S2 are two different 2-D regions defined in terms of FSC and SSC, and F1 and F2 are two more 2-D regions defined in terms of fluorescence parameters, then the logic may be set as Ignore=(S1 AND F1) OR (S2 AND F2). Of course, this is not intended to be a restriction upon only a scatter and a fluorescence gate.

Figure 3:
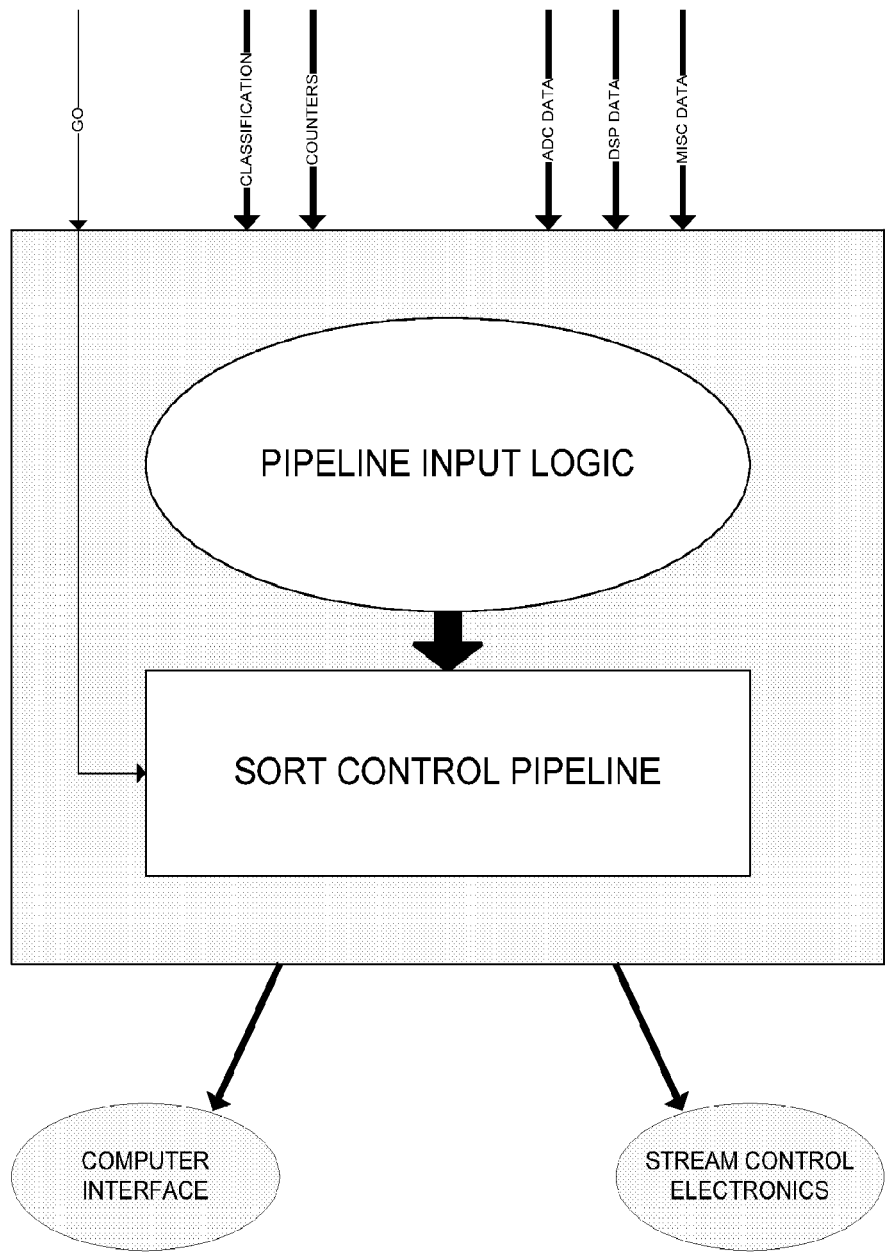
FIG. 3 shows a diagram of currently available architecture.

FIG. 3 shows a diagram of currently available architecture. Sort controller block looks at event classification (i.e., which direction the event should sort to) as well as current counter status (i.e., if the desired sort direction is still actively sorting) before placing an event in the sort pipeline to look for contaminating particles. As an event leaves the pipeline the data values for that event are sent to a computer, and sort stream controlling electronics are provided values to charge the stream and sort a droplet if that event is clear of contaminants nearby. One "workaround" that can be employed with current systems is to raise the system's threshold to the extent that the number of "irrelevant" events is reduced. However, this workaround approach makes events completely invisible for the analysis, which may not be desirable. Also, this workaround approach is not feasible if the population of acceptable coincidence is more fluorescent (or has a higher scatter signal) than a target population. Another method employed in current systems is to use a yield mode of sort decision, in which any instance of a desired target particle population is sorted, regardless of type of contaminating event. However, in one embodiment presented herein, there is provided a means for modification of sort logic, in the context of flow cytometry sorting, to permit deliberate acceptance of a user-specified set (or sets) of events from the decision making process.

Figure 4:
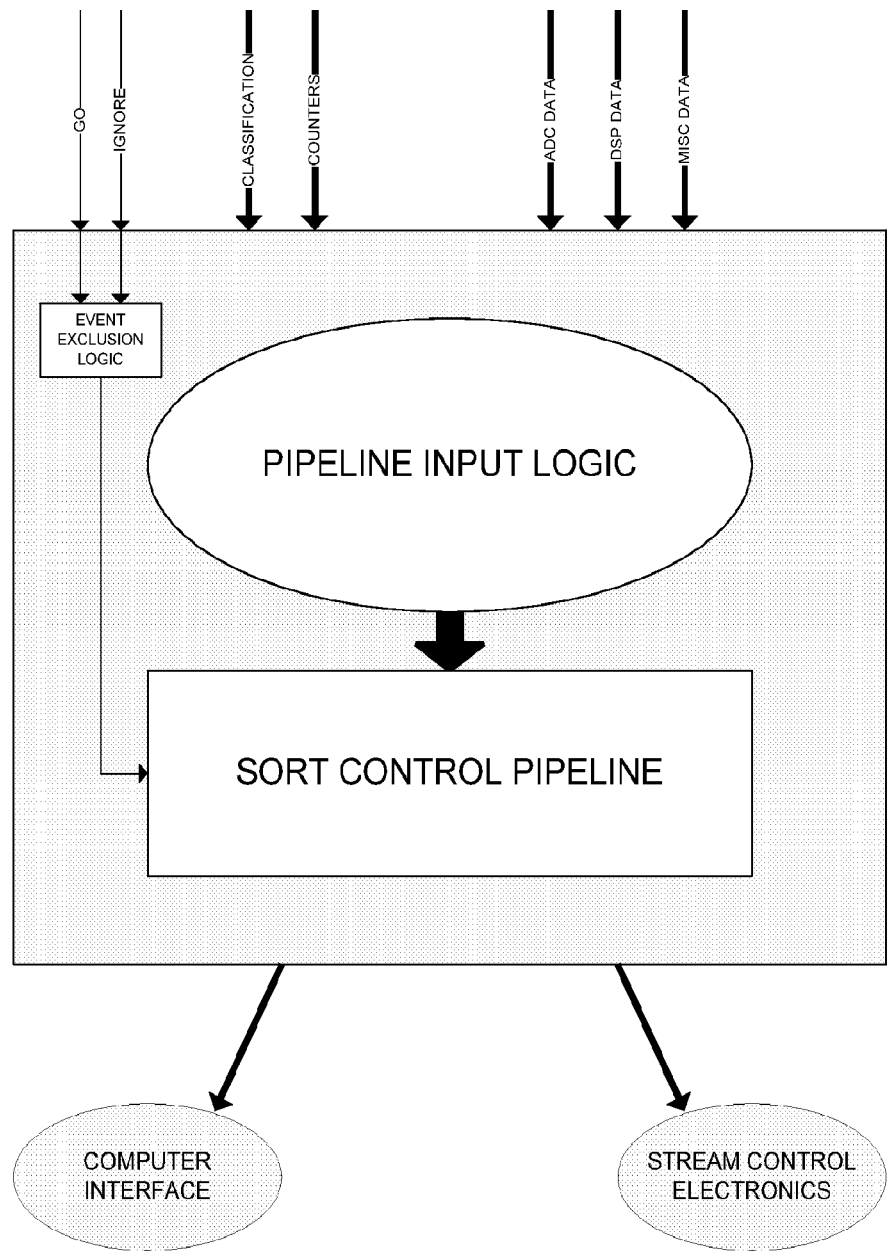
FIG. 4 shows a diagram of an architecture, in accordance with one embodiment presented.

FIG. 4 shows a diagram of an architecture, in accordance with one embodiment presented. Sort controller has a new input value indicating when an event can be accepted by the sort pipeline. For example, and with reference to FIG. 1, an event exclusion logic may be provided in the form of a user-interface for the user to define populations R1 and/or R2 that should be accepted during a subsequent sort analysis. If the event is indicated as an acceptable coincidence event, and that event shows no other sort classification, the event is not placed in the pipeline for consideration as a contaminating particle.

In one embodiment, the user is allowed to draw one or more gates (e.g., AND gates or OR gates) and call out populations that are of acceptable coincidence in the sort logic. For example, a user-interface may be provided for the user to identify populations (e.g., R1 and R2) to be acceptable. If the sort logic sees an event with only this classification bit set, the sort logic will completely ignore the event in the sort pipeline. Since the event does not enter the pipeline, the sort logic for nearby events may allow sorting with the new architecture thereby increasing yield for desired events (i.e., target particles), without sacrificing purity with regard to truly contaminating particles.

For example, in an implementation wherein a user desires to sort stem cells, the user can define specific regions of acceptable coincidence (e.g., marker beads that would not affect purity), while ensuring that unacceptable populations (e.g., cancer cells that would affect purity) are kept out of the sort. Coincidence acceptance gates may be defined in various ways. For example, coincidence acceptance gates may be defined as: 1) A and allow B, wherein A is the target population and B is an acceptable non-target population; or 2) A and NOT C, wherein A is the target population and B is a not acceptable non-target population. In sum, a user is provided the opportunity to make two decisions: 1) identification of the target particle population that is to be sorted; and 2) identification of an acceptable coincidence of non-target particles.

In another embodiment, there is provided a system for sorting particles within a sample. The system may include: (a) a flow cytometer to analyze a sample having a plurality of particle populations, wherein the flow cytometer provides a parameter plot based on the analysis of the sample; (b) a user-interface, wherein a user can define a coincidence acceptance gate in the parameter plot via the user-interface, and wherein the coincidence acceptance gate identifies a non-target particle population in the sample that is to be ignored in a subsequent sort analysis; and (c) a sort analysis system to sort particles within the sample. In one embodiment, the coincidence acceptance gate identifies inert marker beads within the sample. The coincidence acceptance gate may be defined by: (1) a two-dimensional area on the parameter plot; (2) defined by a two parameters on the parameter plot; (3) an area apart from a baseline on the parameter plot; (4) an area apart from a threshold on the parameter plot; and/or any combination or equivalent thereof. The coincidence acceptance gate may also be defined using computer software, or a combination of computer software and firmware (e.g., using a field-programmable gate array).

In another embodiment, there is provided a computer-readable storage medium, having instructions executable by at least one processing device that, when executed, cause the processing device to: (a) analyze a sample having a plurality of particle populations; (b) provide a parameter plot from the analysis of step (a); (c) provide a user-interface wherein a user can define a coincidence acceptance gate in the parameter plot of step (b), and wherein the coincidence acceptance gate identifies a particle population in the sample that is to be ignored in a subsequent sort analysis; and (d) processing the sample through a sort analysis while ignoring the coincidence acceptance gate defined in step (c). In one embodiment, the coincidence acceptance gate identifies inert marker beads within the sample. The coincidence acceptance gate may be defined by: (1) a two-dimensional area on the parameter plot; (2) defined by a two parameters on the parameter plot; (3) an area apart from a baseline on the parameter plot; (4) an area apart from a threshold on the parameter plot; and/or any combination or equivalent thereof. In one embodiment, there is provided a cell sorter comprising such computer-readable storage medium.

In still another embodiment, there is provided a method of sorting particles within a sample, with use of a flow cytometer. The method includes: (a) analyzing a sample having a plurality of particle populations with a flow cytometer; (b) obtaining a parameter plot from the flow cytometry analysis of step (a); (c) defining a coincidence acceptance gate in the parameter plot of step (b), wherein the coincidence acceptance gate identifies a particle population in the sample that may be accepted in a subsequent sort analysis; and (d) processing the sample through a sort analysis. In one embodiment, the coincidence acceptance gate identifies inert marker beads within the sample. The coincidence acceptance gate may be defined by: (1) a two-dimensional area on the parameter plot; (2) defined by a two parameters on the parameter plot; (3) an area apart from a baseline on the parameter plot; (4) an area apart from a threshold on the parameter plot; and/or any combination or equivalent thereof. In one embodiment, there is provided a cell sorter comprising such computer-readable storage medium.

In another embodiment, there is provided a system including: (a) a flow cytometer to analyze a sample, wherein the flow cytometer provides a parameter plot based on the analysis of the sample; (b) a user-interface, wherein a user can define a particle population of disinterest in the parameter plot, and wherein the particle population of disinterest identifies a particle population in the sample that is to be ignored in a subsequent sort analysis; and (c) a sort analysis system to sort particles within the sample, while ignoring the particle population of disinterest in making sort decisions.

In yet another embodiment, there is provided a method of sorting particles within a sample, with use of a flow cytometer. The method includes: (a) identifying a coincidence acceptance gate in a sample, wherein the coincidence acceptance gate identifies a non-target particle population in the sample that is to be ignored in a subsequent sort analysis; (b) flow cytometrically analyzing a sample having a plurality of particle populations; (c) processing the sample through a sort analysis based on the coincidence acceptance gate.

In another embodiment, there is provided a method of sorting particles within a sample, with use of a flow cytometer. The method includes: (a) analyzing a sample having a plurality of particle populations with a flow cytometer; (b) identifying a coincidence acceptance gate in the sample, wherein the particle population of disinterest identifies a non-target particle population in the sample that can be accepted with the target particle population in a subsequent sort analysis; and (c) processing the sample through a sort analysis.

Aspects of the invention include the following clauses:

1. A method of sorting particles within a sample, with use of a flow cytometer, the method comprising:
   (a) analyzing a sample having a plurality of particle populations with a flow cytometer;
   (b) obtaining a parameter plot from the flow cytometry analysis of step (a);
   (c) defining a coincidence acceptance gate in the parameter plot of step (b), wherein the coincidence acceptance gate identifies a non-target particle population that may be accepted with a target particle in a subsequent sort analysis; and
   (d) processing the sample through a sort analysis.

2. The method of Clause 1, wherein the coincidence acceptance gate identifies inert marker beads within the sample.

3. The method of Clauses 1 or 2, wherein the coincidence acceptance gate is defined by a two-dimensional area on the parameter plot.

4. The method of Clauses 1, 2 or 3, wherein the coincidence acceptance gate is defined by a two parameters on the parameter plot.

5. The method of Clauses 1, 2, 3 or 4, wherein the coincidence acceptance gate is defined as an area apart from a baseline on the parameter plot.

6. The method of any of the preceding Clauses, wherein the coincidence acceptance gate is defined as an area apart from a threshold on the parameter plot.

7. The method of any of the preceding Clauses, wherein the coincidence acceptance gate is defined using computer software.

8. The method of any of the preceding Clauses, wherein the coincidence acceptance gate is defined using a combination of computer software and firmware.

9. The method of any of the preceding Clauses, wherein the coincidence acceptance gate is defined using a field-programmable gate array.

10. A system for sorting particles within a sample, the system comprising:
    a flow cytometer to analyze a sample having a plurality of particle populations, wherein the flow cytometer provides a parameter plot based on the analysis of the sample;
    a user-interface, wherein a user can define a coincidence acceptance gate in the parameter plot via the user-interface, and wherein the coincidence acceptance gate identifies a non-target particle population in the sample that may be accepted with a target particle a subsequent sort analysis; and
    a sort analysis system to sort particles within the sample.

11. The system of clause 10, wherein the coincidence acceptance gate identifies inert marker beads within the sample.

12. The system of clause 10 or 11, wherein the coincidence acceptance gate is defined by a two-dimensional area on the parameter plot.

13. The system of clause 10, 11 or 12, wherein the coincidence acceptance gate is defined by a two parameters on the parameter plot.

14. The system of clause 10, 11, 12 or 13, wherein the coincidence acceptance gate is defined as an area apart from a baseline on the parameter plot.

15. The system of any of the preceding Clauses 10 to 14, wherein the coincidence acceptance gate is defined as an area apart from a threshold on the parameter plot.

16. The system of any of the preceding Clauses 10 to 15, wherein the coincidence acceptance gate is defined using computer software.

17. The system of any of the preceding Clauses 10 to 16, wherein the coincidence acceptance gate is defined using a combination of computer software and firmware.

18. The system of any of the preceding Clauses 10 to 17, wherein the coincidence acceptance gate is defined using a field-programmable gate array.

19. A computer-readable storage medium, comprising:
   instructions executable by at least one processing device that, when executed, cause the processing device to
   (a) analyze a sample having a plurality of particle populations;
   (b) provide a parameter plot from the analysis of step (a);
   (c) provide a user-interface wherein a user can define a coincidence acceptance gate in the parameter plot of step (b), and wherein the coincidence acceptance gate identifies a non-target particle population in the sample that may be accepted with a target particle in a subsequent sort analysis; and
   (d) processing the sample through a sort analysis while accepting non-target particles defined by the coincidence acceptance gate.

20. The computer-readable storage medium of clause 19, wherein the coincidence acceptance gate identifies inert marker beads within the sample.

21. The computer-readable storage medium of clause 19 or 20, wherein the coincidence acceptance gate is defined by a two-dimensional area on the parameter plot.

22. The computer-readable storage medium of clause 19, 20, or 21, wherein the coincidence acceptance gate is defined by a two parameters on the parameter plot.

23. The computer-readable storage medium of clause 19, 20, 21 or 22, wherein the coincidence acceptance gate is defined as an area apart from a baseline on the parameter plot.

24. The computer-readable storage medium of any of the preceding Clauses 19 to 23, wherein the coincidence acceptance gate is defined as an area apart from a threshold on the parameter plot.

25. A cell sorter comprising the computer-readable storage medium of clauses 19 to 23.

26. A method of sorting particles within a sample, with use of a flow cytometer, the method comprising:
   (a) identifying a coincidence acceptance gate in a sample, wherein the coincidence acceptance gate identifies a particle population in the sample that is to be ignored in a subsequent sort analysis;
   (b) flow cytometically analyzing a sample having a plurality of particle populations;
   (c) processing the sample through a sort analysis.

27. A method of sorting particles within a sample, with use of a flow cytometer, the method comprising:
   (a) analyzing a sample having a plurality of particle populations with a flow cytometer;
   (b) identifying a coincidence acceptance gate in the sample, wherein the coincidence acceptance gate identifies a non-target particle population in the sample that is acceptable in a subsequent sort analysis; and
   (c) processing the sample through a sort analysis.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

What is claimed is:

1. A method of sorting particles within a sample, with use of a flow cytometer, the method comprising:
   (a) analyzing a sample having a plurality of particle populations with a flow cytometer;
   (b) obtaining a parameter plot from the flow cytometry analysis of step (a);
   (c) defining a coincidence acceptance gate in the parameter plot of step (b), wherein the coincidence acceptance gate identifies a non-target particle population that may be accepted with a target particle in a subsequent sort analysis; and
   (d) processing the sample through a sort analysis.

2. The method of claim 1, wherein the coincidence acceptance gate identifies inert marker beads within the sample.

3. The method of claim 1, wherein the coincidence acceptance gate is defined by a two-dimensional area on the parameter plot.

4. The method of claim 1, wherein the coincidence acceptance gate is defined by a two parameters on the parameter plot.

5. The method of claim 1, wherein the coincidence acceptance gate is defined as an area apart from a baseline on the parameter plot.

6. The method of claim 1, wherein the coincidence acceptance gate is defined as an area apart from a threshold on the parameter plot.

7. The method of claim 1, wherein the coincidence acceptance gate is defined using computer software.

8. The method of claim 1, wherein the coincidence acceptance gate is defined using a combination of computer software and firmware.

9. The method of claim 1, wherein the coincidence acceptance gate is defined using a field-programmable gate array.

10. A system for sorting particles within a sample, the system comprising:
- a flow cytometer to analyze a sample having a plurality of particle populations, wherein the flow cytometer provides a parameter plot based on the analysis of the sample;
- a user-interface, wherein a user can define a coincidence acceptance gate in the parameter plot via the user-interface, and wherein the coincidence acceptance gate identifies a non-target particle population in the sample that may be accepted with a target particle in a subsequent sort analysis;
- a sort analysis system to sort particles within the sample; and
- a computer-readable storage medium, comprising instructions executable by at least one processing device of the system that, when executed, cause the processing device to:
  (a) analyze a sample having a plurality of particle populations;
  (b) provide a parameter plot from the analysis of step (a);
  (c) provide a user-interface wherein a user can define a coincidence acceptance gate in the parameter plot of step (b), and wherein the coincidence acceptance gate identifies a non-target particle population in the sample that may be accepted with a target particle in a subsequent sort analysis; and
  (d) processing the sample through a sort analysis while accepting non-target particles defined by the coincidence acceptance gate.

11. A computer-readable storage medium, comprising:
instructions executable by at least one processing device that, when executed, cause the processing device to
  (a) analyze a sample having a plurality of particle populations;
  (b) provide a parameter plot from the analysis of step (a);
  (c) provide a user-interface wherein a user can define a coincidence acceptance gate in the parameter plot of step (b), and wherein the coincidence acceptance gate identifies a non-target particle population in the sample that may be accepted with a target particle in a subsequent sort analysis; and
  (d) processing the sample through a sort analysis while accepting non-target particles defined by the coincidence acceptance gate.

12. A cell sorter comprising the computer-readable storage medium of claim 11.

13. A method of sorting particles within a sample, with use of a flow cytometer, the method comprising:
  (a) identifying a coincidence acceptance gate in a sample, wherein the coincidence acceptance gate identifies a particle population in the sample that is to be ignored in a subsequent sort analysis;
  (b) flow cytometrically analyzing a sample having a plurality of particle populations;
  (c) processing the sample through a sort analysis.

14. A method of sorting particles within a sample, with use of a flow cytometer, the method comprising:
  (a) analyzing a sample having a plurality of particle populations with a flow cytometer;
  (b) identifying a coincidence acceptance gate in the sample, wherein the coincidence acceptance gate identifies a non-target particle population in the sample that is acceptable in a subsequent sort analysis; and
  (c) processing the sample through a sort analysis.

* * * * *